(12) United States Patent
Moriyama et al.

(10) Patent No.: US 7,993,602 B2
(45) Date of Patent: Aug. 9, 2011

(54) STERILIZING CONTAINER AND ENDOSCOPIC SYSTEM

(75) Inventors: Hiroki Moriyama, Tokyo (JP);
Takehiro Nishiie, Tokyo (JP); Atsushi Watanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 1220 days.

(21) Appl. No.: 11/416,008

(22) Filed: May 1, 2006

(65) Prior Publication Data

US 2006/0193761 A1    Aug. 31, 2006

Related U.S. Application Data

(63) Continuation of application No. PCT/JP2004/016876, filed on Nov. 12, 2004.

(30) Foreign Application Priority Data

Nov. 12, 2003  (JP) ................. 2003-382964

(51) Int. Cl.
*A61L 2/07* (2006.01)
(52) U.S. Cl. .................. 422/292; 400/300
(58) Field of Classification Search ............... 600/156; 422/26, 28, 292, 300
See application file for complete search history.

(56) References Cited

U.S. PATENT DOCUMENTS

| | | | | | |
|---|---|---|---|---|---|
| 4,671,943 | A | * | 6/1987 | Wahlquist | 422/300 |
| 4,783,321 | A | * | 11/1988 | Spence | 422/300 |
| 5,424,048 | A | * | 6/1995 | Riley | 422/300 |
| 5,792,422 | A | * | 8/1998 | Lin et al. | 422/31 |
| 6,594,971 | B1 | * | 7/2003 | Addy et al. | 53/413 |
| 2001/0023001 | A1 | | 9/2001 | Weiss et al. | |
| 2002/0015673 | A1 | | 2/2002 | Moriyama | |
| 2003/0133830 | A1 | | 7/2003 | Gonzalez et al. | |

FOREIGN PATENT DOCUMENTS

JP   2000-051323   2/2000
JP   2002-45335    2/2002

* cited by examiner

*Primary Examiner* — Sean E Conley
(74) *Attorney, Agent, or Firm* — Scully, Scott, Murphy & Presser, P.C.

(57) ABSTRACT

A sterilizing container houses an endoscope having openings and an inner region communicating with the openings at a time of an autoclave sterilization. In the sterilizing container, a gap portion of a predetermined volume is formed at a position to which the opening faces when the endoscope is housed in the sterilizing container, and a steam entrance path, which communicates the gap portion with an outside space of the sterilizing container, is formed so as to guide steam fed from the outside space at the sterilization to the inner region of the endoscope via the gap portion and the openings.

9 Claims, 7 Drawing Sheets

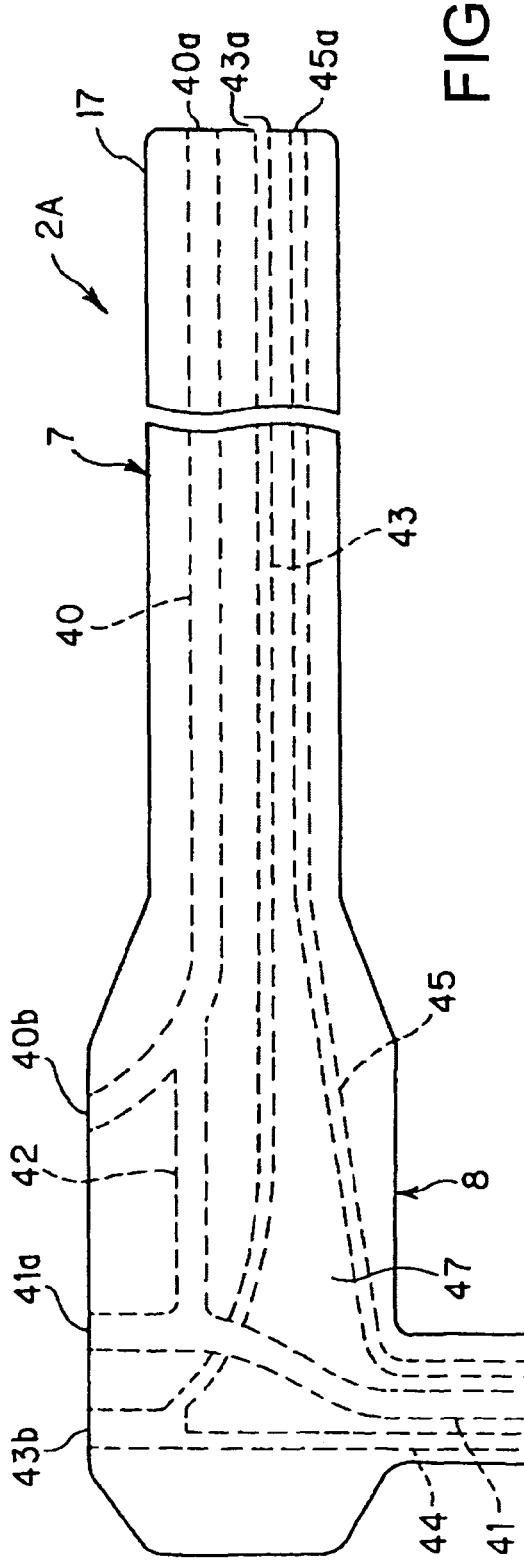
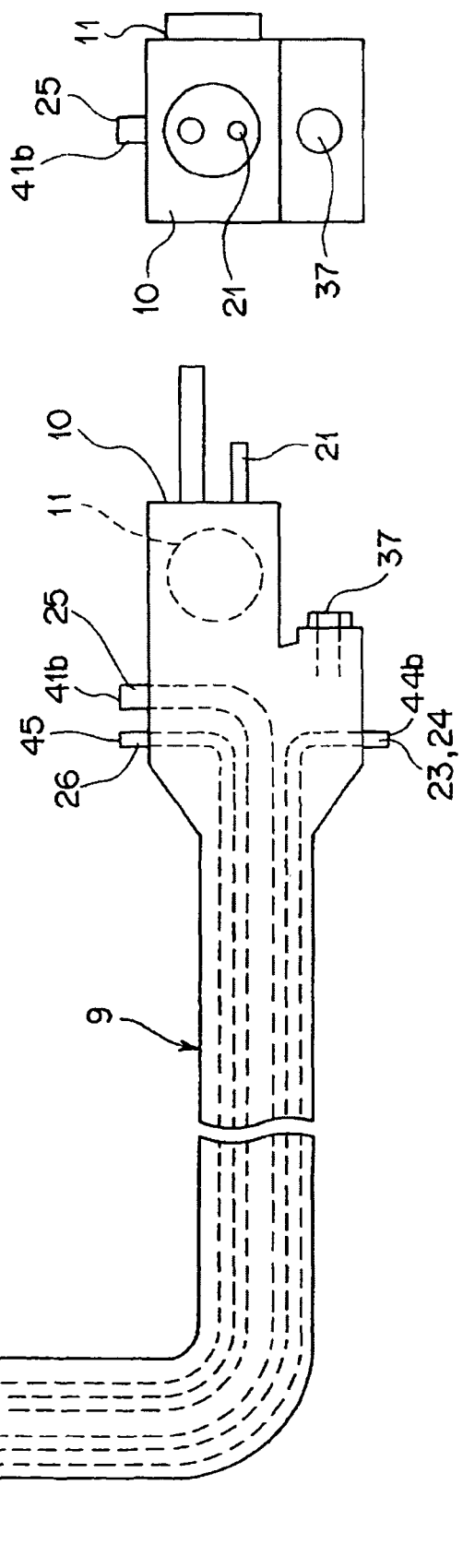

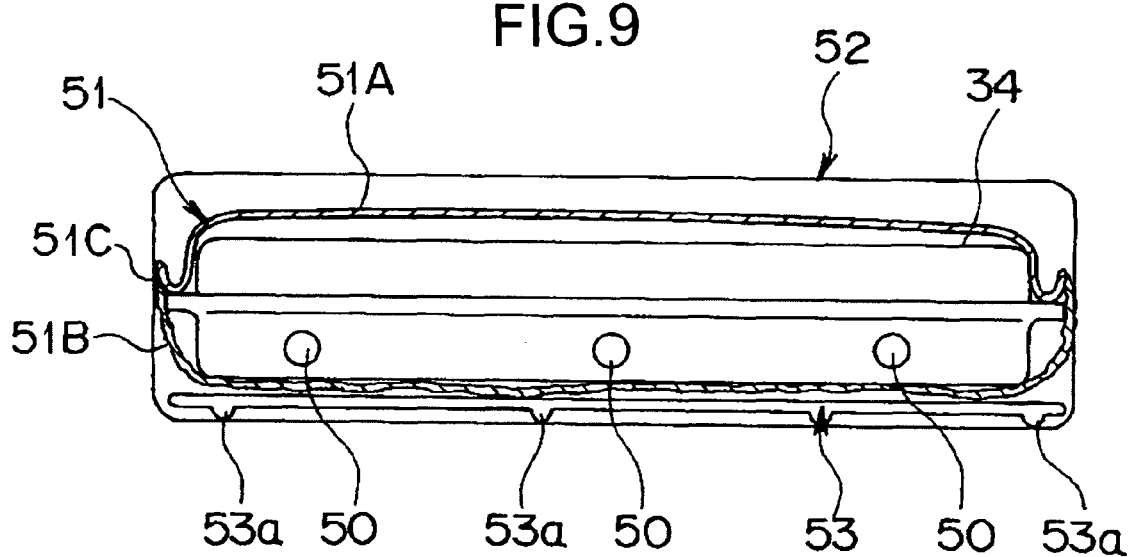
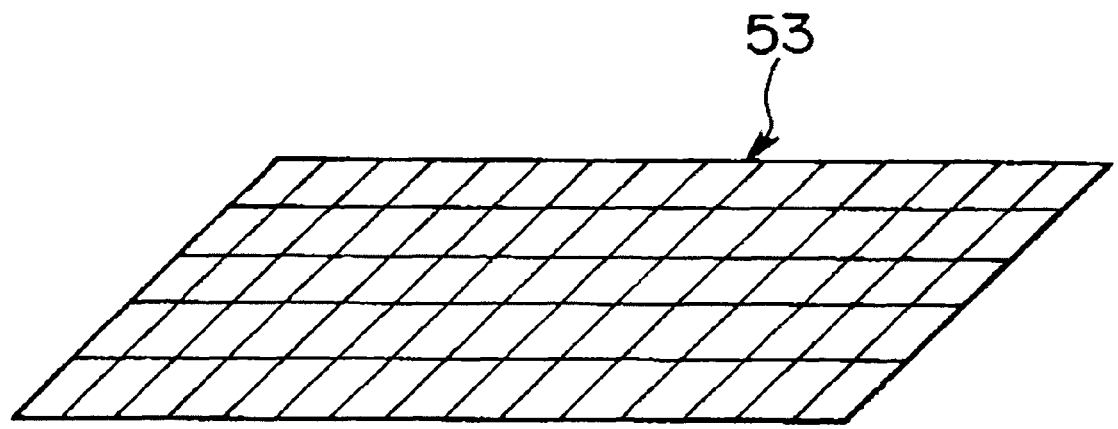

STERILIZING CONTAINER AND ENDOSCOPIC SYSTEM

CROSS-REFERENCE TO RELATED APPLICATIONS

This application is a continuation of PCT international application Ser. No. PCT/JP2004/016876 filed Nov. 12, 2004 which designates the United States, incorporated herein by reference, and which claims the benefit of priority from Japanese Patent Application No. 2003-382964, filed Nov. 12, 2003, incorporated herein by reference.

BACKGROUND OF THE INVENTION

1. Field of the Invention

The present invention relates to a sterilizing container that houses an endoscope at a time of sterilization of the endoscope by high-temperature and pressure steam, and an endoscopic system including the sterilizing container.

2. Description of the Related Art

Conventionally, the endoscopes are widely used in the field of medicine since the endoscopes allow for observations of deep parts of body cavities when inserted into the body cavities or the like, and allow for medical treatments or the like when used together with medical appliances as necessary.

Endoscopes for medical uses are required to be disinfected and sterilized without fail after the use for the prevention of infection or the like.

In recent years, autoclave sterilization (sterilization with high-temperature and pressure steam) has come to be widely used as a mainstream sterilization method of endoscope-related apparatus, since the autoclave sterilization does not accompany cumbersome procedures when used for the disinfection and sterilization; the sterilized apparatus can be used immediately after the sterilization; and the autoclave sterilization has an advantageous running cost.

For example, Japanese Patent Application Laid-Open No. 2000-51323 describes a conventional example of sterilization treatment which is employed for the sterilization of the endoscope by high-temperature and pressure steam and which serves to prevent damages on an outer cladding of the endoscope from being caused by a difference in pressures inside and outside the endoscope.

SUMMARY OF THE INVENTION

A sterilizing container according to one aspect of the present invention houses an endoscope having openings and an inner region communicating with the openings at a time of an autoclave sterilization. In the sterilizing container, a gap portion of a predetermined volume is formed at a position to which the opening faces when the endoscope is housed in the sterilizing container, and a steam entrance path, which communicates the gap portion with an outside space of the sterilizing container, is formed so as to guide steam fed from the outside space at the sterilization to the inner region of the endoscope via the gap portion and the openings.

An endoscopic system according to another aspect of the present invention includes an endoscope having openings and an inner region communicating with the openings, and a sterilizing container housing the endoscope at a time of an autoclave sterilization. In the sterilizing container, a gap portion of a predetermined volume is formed at a position to which the opening faces when the endoscope is housed in the sterilizing container, and a steam entrance path, which communicates the gap portion with an outside space of the sterilizing container, is formed so as to guide steam fed from the outside space at the sterilization to the inner region of the endoscope via the gap portion and the openings.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 2A and 2B are schematic views of a channel system of an endoscope shown in FIG. 1;

FIG. 9 is a schematic view of a modified example of the third embodiment and shows the sterilizing package housed in a chamber; and FIG. 10 is a perspective view of an example of a base member shown in FIG. 9.

DETAILED DESCRIPTION OF THE PREFERRED EMBODIMENTS

Embodiments of the present invention will be described below with reference to the accompanying drawings.

Figure 1:
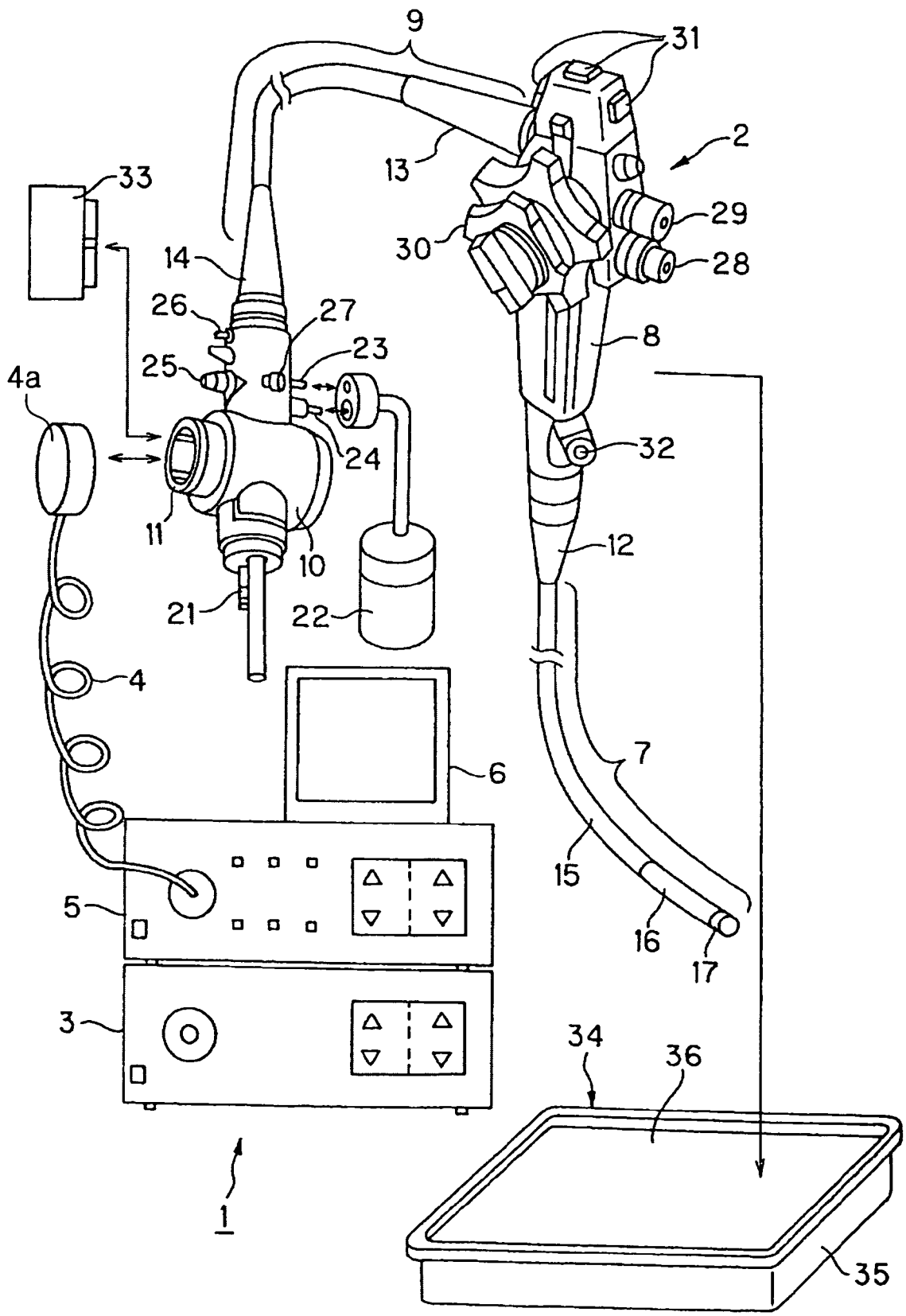
FIG. 1 is a schematic view of an overall structure of an endoscopic system according to a first embodiment of the present invention.
Figure 3A:
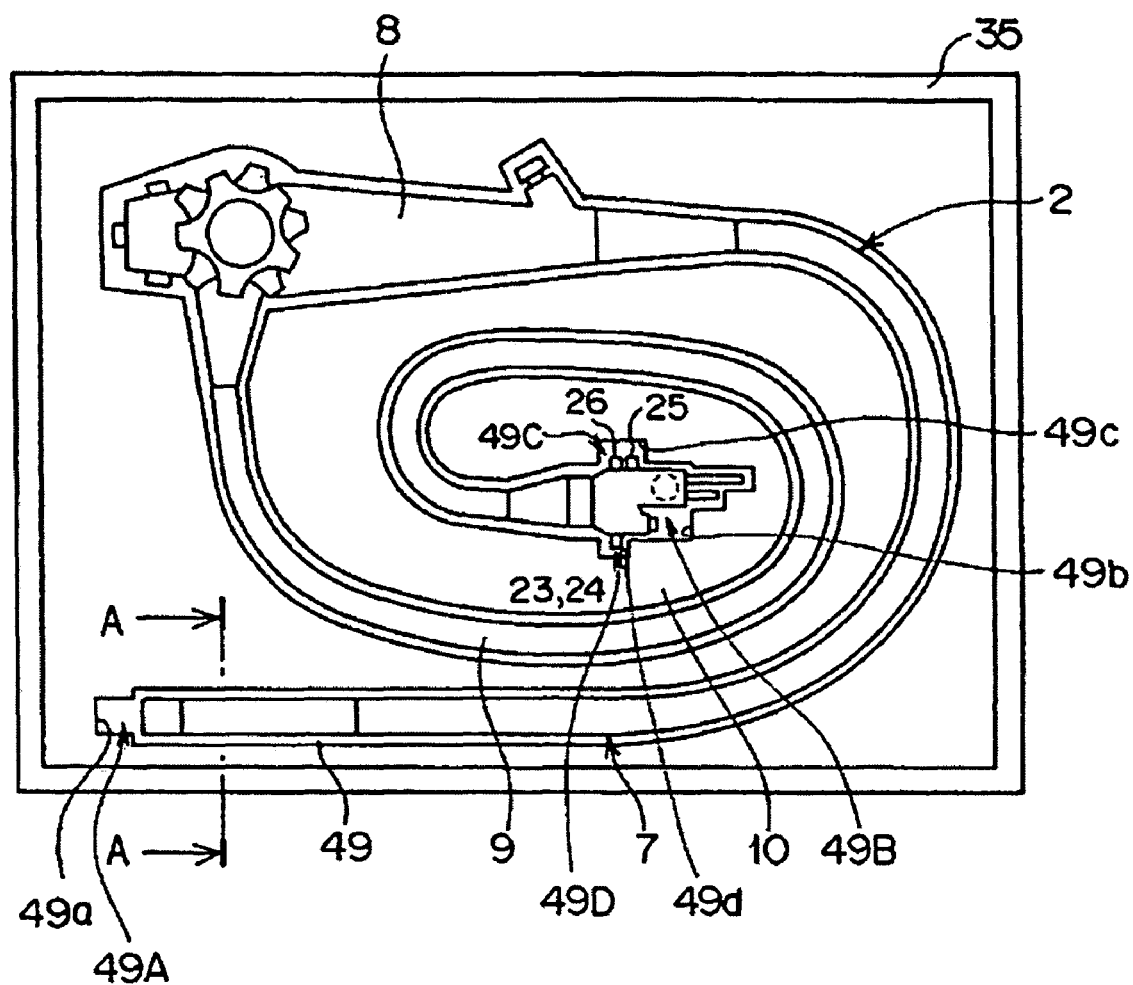
FIG. 3A is a plan view of the endoscope housed in a tray.
Figure 3B:
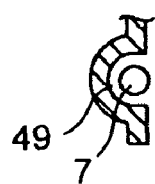
FIG. 3B is a cross-sectional view taken along line A-A of FIG. 3A.
Figure 4A:
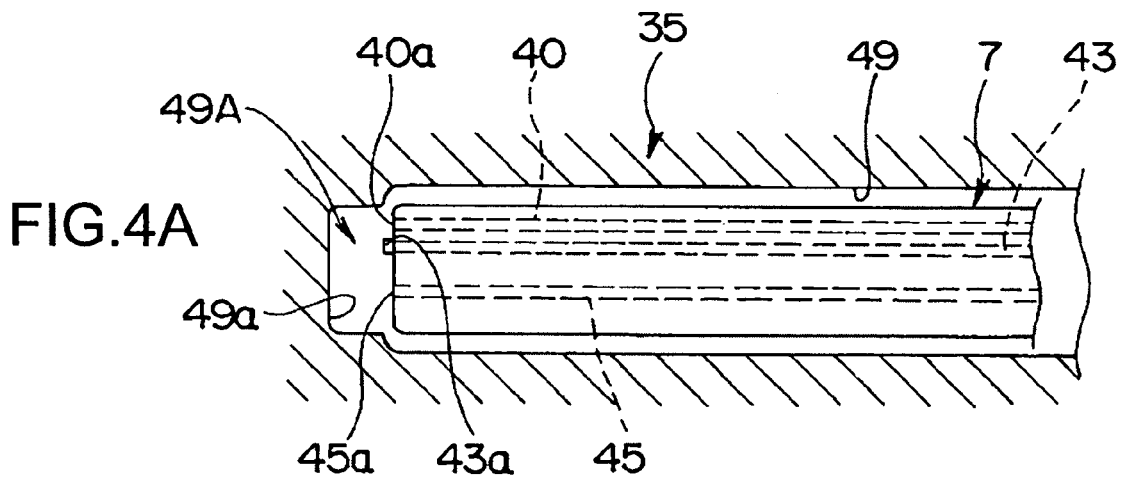
FIG. 4A is a enlarged plan view of near the restricting portion near a tip portion of an insertion in a state where main parts of the endoscope shown in FIG. 3A is housed in a restricting portion of the tray.
Figure 4B:
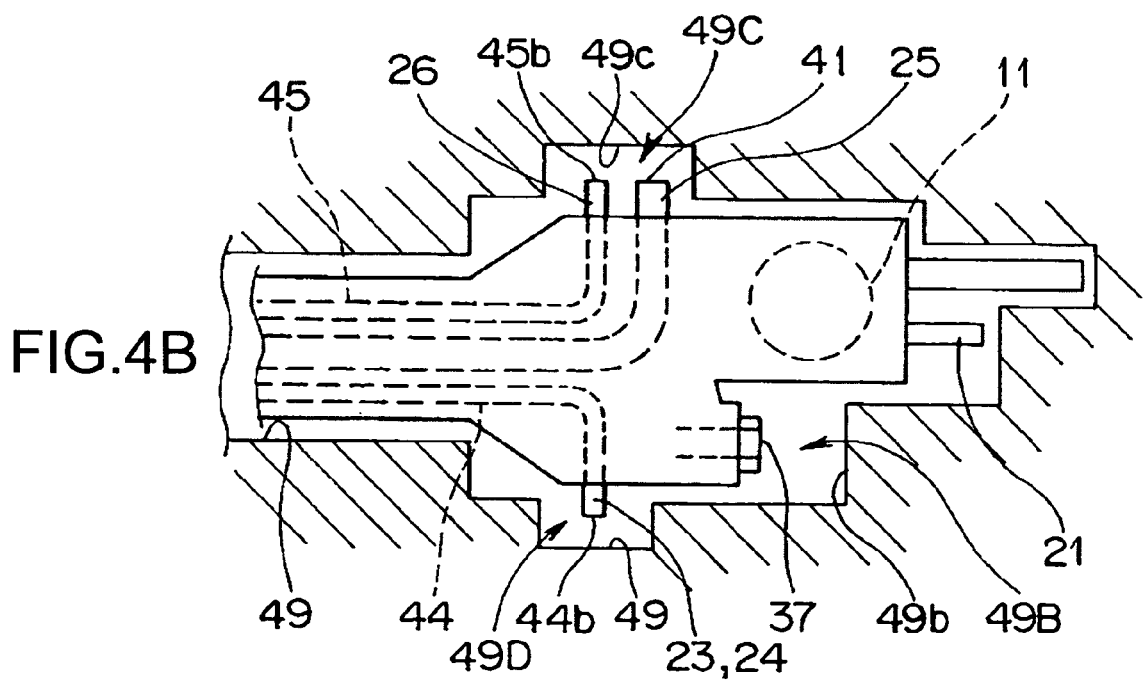
FIG. 4B is a enlarged plan view of near the restricting portion near a connector in the state.

FIGS. 1, 2A, 2B, 3A, 3B, 4A and 4B show an endoscopic system according to a first embodiment of the present invention. FIG. 1 is a schematic view of an overall structure of the endoscopic system; FIG. 2A and 2B are schematic views of a channel system of an endoscope shown in FIG. 1; FIG. 3A is a plan view of the endoscope housed in a tray; FIG. 3B is a cross-sectional view taken along line A-A of FIG. 3A; and FIGS. 4A and 4B are enlarged plan views of main parts of the endoscope shown in FIG. 3A housed in a restricting portion of the tray, where FIGS. 4A and 4B show the restricting portion near a tip portion of an insertion, and the restricting portion near a connector, respectively.

As shown in FIG. 1, an endoscopic system 1 which is employed for an endoscopic inspection includes an endoscope 2 that has an imaging unit, a light source 3 that is detachably connected to the endoscope 2 to supply illuminating light to a light guide of the endoscope 2, a video processor 5 that is connected to the endoscope 2 via a cable 4 to control the imaging unit of the endoscope 2 and to process a signal obtained from the imaging unit, and a monitor 6 that displays an image corresponding to an object image supplied from the video processor 5.

The endoscope 2 is made from a material having resistance to high-temperature and pressure steam so that the endoscope 2 can be subjected to sterilizing treatment by high-temperature and pressure steam after being used for the endoscopic inspection such as observation or treatment and cleaned. Further, the endoscope 2 is structured so that the high-temperature and pressure steam can be actively (forcibly) guided for the sterilizing treatment into a space 47 (see FIG. 2A), which is a region inside jackets (covers) of an insertion 7 and an operating unit 8 of the endoscope 2 as described later, and therefore a component such as a signal line inside the endoscope is also made from a member which has resistance to the high-temperature and pressure steam.

The endoscope 2 includes the elongated flexible insertion 7, the operating unit 8 that is connected to a proximal end of the insertion 7, a flexible connection code (universal code) 9 that extends from a side of the operating unit 8, a connector 10 that is provided at an end of the connection code 9 and detachably connected to the light source 3, an electrical connector 11 that is provided at an end of the connector 10 and detachably connectable to a connector 4a provided at an end of the signal cable 4 which is detachably connected to the video processor 5.

The electrical connector 11 has a ventilating opening 37 which communicates inside of the endoscope 2 with an outside space as shown in FIGS. 2A and 2B. More specifically, the ventilating opening 37 serves to communicate a space around external surfaces of channels 40 to 45 described later and the outside space of the endoscope 2.

At a connecting portion between the insertion 7 and the operating unit 8, an insertion-side anti-breaking member 12 is provided which includes an elastic member for preventing a sharp bending of the connecting portion. At a connecting portion between the operating unit 8 and the connection code 9, a similar operating unit-side anti-breaking member 13 is provided; and at a connecting portion between the connection code 9 and the connector 10, a similar connector-side anti-breaking member 14 is provided.

The insertion 7 is formed from a flexible piping 15 which is flexible and soft, and a curved portion 16 which is provided at a tip side of the flexible piping 15 and can be made bent by an operation through the operating unit 8, and a tip portion 17 which is provided at a tip of the insertion 7, and an observation optical system, an illuminating optical system, or the like not shown are provided on the tip portion 17.

The tip portion 17 is provided with a gas and fluid-delivery nozzle that injects washing liquid or a gas towards optical components provided on an external surface of the observation optical system not shown according to a gas-delivery operation and a liquid-delivery operation, and a suction mouth which is an opening at a tip end side of a treatment-apparatus channel not shown which is provided to receive and let through the apparatus arranged in the insertion 7 and to suction liquid inside the body cavity. Further, the tip portion 17 has a liquid-delivery mouth which is open towards an observation object and serves to inject the liquid thereto.

The connector 10 is provided with a gas-feed mouth 21 which is detachably connected to a gas-feed source (not shown) embedded in the light source 3, a liquid-delivery-tank pressurizing mouth 23 which is detachably connected to a liquid-delivery tank 22 as a liquid source, and a gas-feed mouth 24. Further, on an opposite side of the connector 10 from the liquid-delivery-tank pressurizing mouth 23 and the gas-feed mouth 24, a suction mouth 25 connected to a suction source (not shown) is provided so as to perform a suction operation through a suction hole. Further, near the suction mouth 25, a feed mouth 26 is provided and connected to liquid-delivery means that is not shown and serves to feed a liquid through a liquid-delivery hole. Further, on another side surface of the connector 10, an earth-terminal mouth 27 is provided so as to feedback a leakage current to a radiofrequency treatment apparatus when radiofrequency leakage current is generated in the endoscope at a radiofrequency treatment or the like.

The operating unit 8 has a gas and liquid-delivery operation button 28 for controls of the gas-delivery operation and the liquid-delivery operation, a suction operation button 29 for controls of the suction operation, a bending operation knob 30 for controls of a bending operation of the curved portion, plural remote switches 31 for remote controls of the video processor 5, and an apparatus insertion mouth 32 which is an opening that communicates with the treatment-apparatus channel.

A water-proof cap 33 can be detachably connected to the electrical connector 11 of the endoscope 2. The water-proof cap 33 is provided with a pressure control valve not shown. Further, a sterilizing container 34 is employed at a time of the high-pressure steam sterilization of the endoscope 2 as shown in FIG. 1.

The sterilizing container 34 includes a tray 35 which serves as a tray for the endoscope and houses the endoscope 2 to be sterilized, and a lid member 36 which covers an upper side of the tray 35. The tray 35 and the lid member 36 are provided with plural ventilation holes not shown, and the steam can pass through these ventilation holes. Details of the structure of the sterilizing container 34 will be described later.

FIGS. 4A and 4B are schematic views of various channels embedded inside the endoscope 2. As shown in FIGS. 4A and 4B, the connector 10 of the endoscope 2 according to the embodiment is provided with the ventilating opening 37 which serves as a hole or an opening that communicates the inside space of the endoscope 2 with the outside space. Through the ventilating opening 37, the outside space of the endoscope 2 is communicated with an inside space 47 sealed by an outer cladding portion of the endoscope 2. Though not shown, a filter may be provided on a part of the ventilating opening 37, and the filter may have plural small holes that let the steam through but not matters larger than the steam.

Further, the connector 10 is provided with the liquid-delivery-tank pressurizing mouth 23, the gas-feed mouth 24, the suction mouth 25, and the feed mouth 26 as shared holes/openings that communicate with various channels embedded inside the endoscope 2. With those openings, various channels inside the endoscope 2 are made to communicate with the outside space of the endoscope 2.

In the present embodiment, the high-temperature and pressure steam is made to flow into the space 47 through the ventilating opening 37 at the high-temperature and pressure steam sterilization treatment, whereby an external side, which is exposed to the space 47, of the channel such as the gas and liquid-delivery channel can be sterilized by the high-temperature and pressure steam in a short time period. Further, the high-temperature and pressure steam is made to flow inside the respective channels inside the endoscope 2 from the liquid-delivery-tank pressurizing mouth 23, the gas-feed mouth 24, the suction mouth 25, and the feed mouth 26 described above, whereby an internal sides of the respective channels communicating with the openings can be sterilized by the high-temperature and pressure steam in a short time period.

Respective channels are arranged as shown in FIG. 4A. A channel 40 is mainly inside the insertion 7, and a channel tip end 40*a* thereof is open towards the outside space at the tip portion 17, whereas a channel back end 40*b* thereof is open towards the outside space at the operating unit 8. The channel 40 is, for example, a channel for the insertion of the treatment apparatus or a channel for the suction.

A channel 41 is mainly inside the connection code 9, and a channel tip end 41*a* thereof is open towards the outside space at the operating unit 8, whereas a channel back end 41*b* thereof is open towards the outside space at the connector 10 with the suction mouth 25. The channel 41 is, for example, a channel for suction.

A channel 42 is mainly inside the operating unit 8, and a channel tip end thereof is common to the channel back end 41*a* and open towards outside at the operating unit 8. The channel 42 is, for example, a channel for suction.

When a piping extending from a suction apparatus not shown is connected with the channel back end 41*b* (suction mouth 25), and the suction operation is performed by the suction apparatus, with the channel tip end 41*a* and the channel back end 40*b* closed, the suction can be realized through the channel tip end 40*a* through a path formed by the channels 41, 42, and 40.

A channel 43 is mainly inside the insertion 7, and a channel tip end 43*a* thereof is open towards the outside space at the tip portion 17, whereas a channel back end 43*b* thereof is open towards the outside space at the operating unit 8. The channel 43 is, for example, a channel for gas and liquid delivery which delivers gases or liquids for cleaning a lens surface.

A channel 44 is mainly inside the connection code 9, and a channel tip end thereof is common to the channel back end 43*b*, and open towards the outside space at the operating unit 8, whereas a channel back end 44*b* thereof is open towards the outside space at the connector 10 via the liquid-delivery-tank pressurizing mouth 23 and the gas feed mouth 24. When the back end 43*b* is closed and a gas or liquid is delivered from the back end 44*b* (i.e., the liquid-delivery-tank pressurizing mouth 23, gas feed mouth 24), the gas or liquid delivery can be realized through the channel tip end 43*a*.

A channel 45 is mainly inside the insertion 7 and the connection code 9, and a channel tip end 45*a* thereof is open towards the outside space at the tip portion 17, whereas a channel back end 45*b* thereof is open towards the outside space at the connector 10 via the feed mouth 26. The channel 45 is, for example, a channel that delivers liquid forwards, i.e., to the observation object.

Thus, various channels are embedded in the endoscope 2, and each channel is open to the outside space at both ends and liquid or the like can flow through inside the channel. Further, the insertion 7 and the connection code 9 are both formed from a soft material, and hollow not solid. Further, most of the channels are arranged in a space inside the insertion 7 and the connection code 9 without being fixed thereto so that the channels can move flexibly, and the channels are surrounded mostly by space though there are other components embedded in the endoscope.

Middle portions (here, "middle portion" means a position away from the ends and corresponds to a relatively wide range) of the external sides of the channels (and an internal side of the cladding of the endoscope 2) are exposed to the surrounding space 47, and the surrounding space 47 communicates with the outside space through the ventilating opening 37. In other words, the external sides of the channels are exposed to the outside space via the ventilating opening 37 which communicates with the space 47 (in other words, serves as communicating means). It is possible to select whether to put the channels in the communicating state through the ventilating opening 37 or not with the attachment/detachment (removal) of a water-proof cap not shown.

In the present embodiment, a space around the middle portion of the path which connects two ends of the channel, for example, is not filled with a filler or a solid material and the space inside the outer cladding of the endoscope 2 is left void, so as to form the space 47. Along the path that connects the space 47 and the ventilating opening 37, various components or parts are embedded, though in a manner so as not to block the flow of the steam. Thus, the steam can pass through the path without being obstructed.

In the endoscope 2 according to the present embodiment, since the ventilating opening 37 is provided, the surrounding space 47 of the channels inside the endoscope 2 can be made to communicate with the outside space at the sterilizing treatment, and further, the space 47 can be set to a prevacuum state at a prevacuum treatment. Still further, since openings such as the liquid-delivery-tank pressurizing mouth 23, the gas-feed mouth 24, the suction mouth 25, and the feed mouth 26, are provided to the channels, the insides of the channels in the endoscope 2 can be made to communicate with the outside space at the sterilization treatment, and further, the space inside the channels can be set to a prevacuum state at the prevacuum treatment.

In other words, in the endoscope 2, the high-temperature and pressure steam can be swiftly fed to and fill inside the channels as well as the space 47 outside the channels in the subsequent high-temperature and pressure steam sterilization process, so as to finish the high-temperature and pressure steam sterilization treatment in a short time.

Here, in the endoscopic system of the present embodiment, even when the endoscope 2 is housed in the tray 35 of the sterilizing container 34, the entrance of the steam inside the endoscope from the openings of the channels or from the ventilating opening 37 that serve as entrance holes for the steam, is not obstructed, whereby the sterilization of the channels embedded in the endoscope 2 can be swiftly and securely performed.

FIG. 3A shows the endoscope 2 housed in the tray 35 of the sterilizing container 34. As shown in FIG. 3A, the tray 35 includes a restricting portion 49 where a depression is formed corresponding to the shape of the endoscope 2 so that the endoscope 2 can be fit and accommodated into the depression. For example, a section taken along line A-A of FIG. 3A looks like FIG. 3B. The restricting portion 49 is formed as a depression of a slightly larger shape than the shape of the respective portions of the endoscope 2 so that the respective portions are properly accommodated into predetermined positions.

In the present embodiment, the restricting portion 49 includes a first to a fourth restricting areas 49*a* to 49*d* corresponding to the channel tip ends 40*a*, 43*a*, and 45*a* serving as the channel openings in the tip portion 17 of the insertion 7, the ventilating opening 37 serving as the steam entrance hole, the suction mouth 25 and the feed mouth 26 serving as the channel openings (channel back ends 41*b* and 45*b*), and the liquid-delivery-tank pressurizing mouth 23 and the gas-feed mouth 24 serving as the channel openings (channel back end 44*b*), respectively.

The first to the fourth restricting areas 49*a* to 49*d* are formed with clearances 49A to 49D, respectively, so that a cross-sectional area of each restricting area is larger than the cross-sectional area of the opening. Here, "cross-sectional area . . . larger than the cross-sectional area of the opening" means, for example, that a plane which is perpendicular to a direction of entrance of the steam fed from outside at the time of the autoclave sterilization is larger than the section of the opening at each of the clearances 49A to 49D.

Further, in the present embodiment, a gap formed between inner surfaces of the restricting portion 49 and the endoscope 2, other than the clearances 49A to 49D serves as a steam entrance path. The steam entrance path serves to communicate the clearances 49A to 49D and the outside space of the sterilizing container 34; the steam entrance path also serves to guide the steam fed from outside the sterilizing container 34 at the time of autoclave sterilization to an inner area of the endoscope 2 through the clearances 49A to 49D and the corresponding openings of the endoscope 2 (channel tip end 40*a*, ventilating opening 37, or the like described later).

Though in the present embodiment, the steam entrance path is formed from a part of the restricting portion 49, the steam entrance path may be formed separately from the restricting portion 49 from separate piping or the like. In other words, the steam entrance path can be realized by any structures as far as the structure allows the communication between the clearances 49A to 49D and the outside space of the sterilizing container 34.

Preferably, the cross-sectional area of the steam entrance path (i.e., an area of the plane perpendicular to the direction of the entrance of steam) is larger than the cross-sectional area of the corresponding opening of the endoscope 2. Further, when a single clearance communicates with the outside space of the sterilizing container 34 via plural steam entrance paths, the sum of the cross-sectional areas of the plural steam entrance paths is preferably larger than the cross-sectional area of the opening corresponding to the clearance.

Further, the structure of the restricting portion 49 is not necessarily limited to the structure shown in FIGS. 3A and 3B. In other words, the minimum requirement of the function of the restricting portion 49 is that the restricting portion 49 can fix the position of the endoscope 2 so that the openings (channel tip end 40*a* described later, for example) face with the clearances 49A to 49D. As far as the restricting portion 49 can realize such function, the restricting portion 49 may be formed by any structure. The restricting portion 49 may be formed separately from the clearances 49A to 49D.

FIG. 4A shows the restricting portion near the tip portion of the insertion, whereas FIG. 4B shows the restricting portion near the connector. As shown in FIG. 4A, the first restricting area 49*a* accommodates the tip portion 17 of the insertion while maintaining the clearance 49A. The channel tip ends 40*a*, 43*a*, and 45*a* (also referred to as channel openings) of the tip portion 17 are accommodated at positions where the steam easily enters as the tip ends are arranged in front of the clearance 49A and exposed to the external side of the tray 35.

As shown in FIG. 4B, the second restricting area 49*b* accommodates the ventilating opening 37 of the electrical connector 11 while maintaining the clearance 49B. The ventilating opening 37 is accommodated at a position where the steam easily enters since the ventilating opening 37 is arranged in front of the clearance 49B and exposed to the external side of the tray 35.

The third restricting area 49*c* accommodates the openings (channel back ends 41*b* and 45*b*) of the suction mouth 25 and the feed mouth 26 while maintaining the clearance 49C. The openings (channel back ends 41*b* and 45*b*) are accommodated at positions where the steam easily enters since the openings are arranged in front of the clearance 49C and exposed to the external side of the tray 35.

The fourth restricting area 49*d* accommodates the opening (channel back end 44*b*) of the liquid-delivery-tank pressurizing mouth 23 and the gas-feed mouth 24 while maintaining the clearance 49D. The opening (channel back end 44*b*) is accommodated at a position where the steam easily enters since the opening is arranged in front of the clearance 49D and exposed to the external side of the tray 35.

It is sufficient if the first to the fourth restricting areas 49*a* to 49*d* are arranged and formed so as to correspond to the endoscope 2 to be housed in the tray 35, and if each of the clearances 49A to 49D is formed so as to have a larger cross-sectional area than the corresponding opening of the endoscope 2.

Advantageous effects of the arrangement of the first to the fourth restricting areas 49*a* to 49*d* of the present embodiment will be described. Since the tray 35 of the present embodiment includes the first to the fourth restricting areas 49*a* to 49*d* that accommodate the openings (channel back ends 44*b*, 41*b*, and 45*b*) of the channels and the ventilating opening 37 of the endoscope 2, and the clearances 49A to 49D are formed so as to have larger cross-sectional areas than the corresponding openings of the first to the fourth restricting areas 49*a* to 49*d*, the clearances 49A to 49D and the steam entrance path are provided facing the external side of the tray 35. Hence, the high-temperature and pressure steam can more easily enter inside the channels and the space 47 outside the channels at the sterilization treatment, whereby the permeability can be improved over that of the tray without clearances.

Specifically, since the high-temperature and pressure steam swiftly fills inside the channels and the space 47, the pressure inside the channels and the space 47 rises to raise the temperature. Further, since the high-temperature and pressure steam swiftly fills the middle portion of the channels, the pressure in the middle portion of the channels rises to raise the temperature. Thus, with the smooth temperature rise, the high-temperature and pressure steam sterilization can be performed without fail in a short time.

Thus, according to the endoscopic system of the present embodiment, since the restricting areas 49*a* to 49*d* with the clearances 49A to 49D are provided, even when the endoscope 2 is accommodated inside the tray 35, the entrance of steam inside the endoscope via the openings (channel back ends 44*b*, 41*b*, and 45*b*) of the channels and the ventilating opening 37, which serves as the steam entrance hole, is not obstructed, and the sterilization inside the channels embedded in the endoscope 2 can be swiftly performed without fail.

Figure 5:
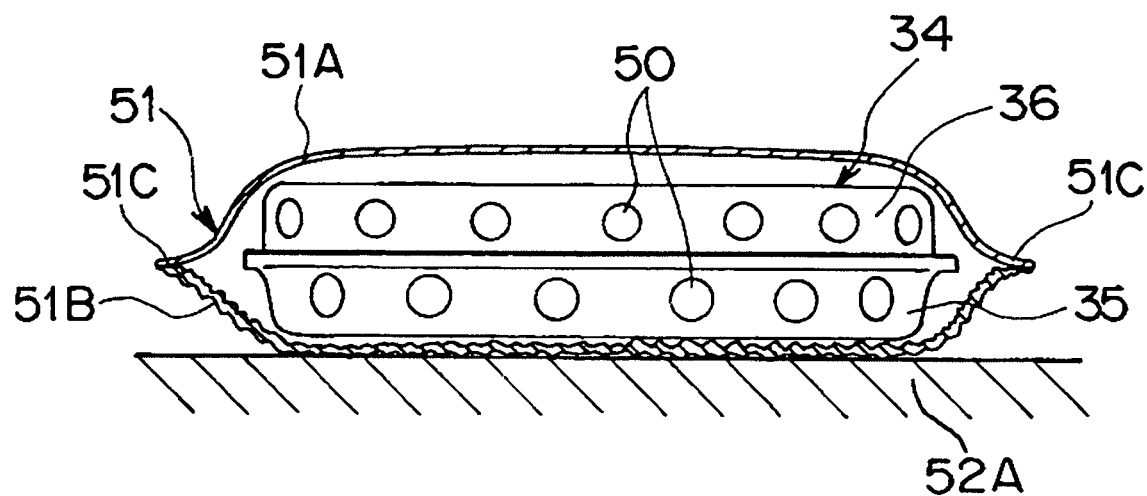
FIG. 5 is a schematic view of a structure of a sterilizing container used in an endoscopic system according to a second embodiment of the present invention.
Figure 6:
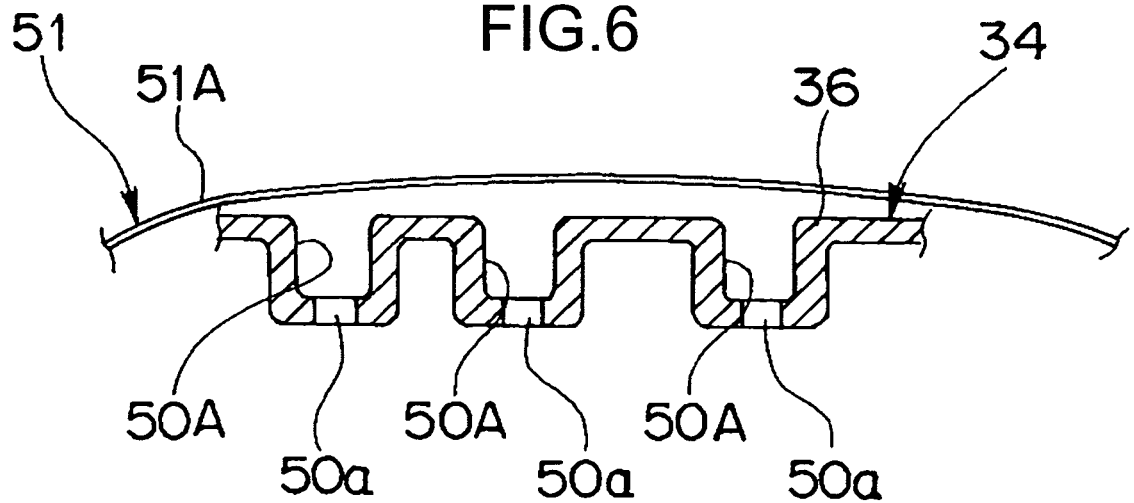
FIG. 6 is a schematic view of a modified example of the sterilizing container shown in FIG. 5.

FIGS. 5 and 6 show an endoscopic system according to a second embodiment of the present invention. FIG. 5 is a schematic view of a structure of a sterilizing container employed in the endoscopic system, and FIG. 6 is a schematic view of a modified example of the sterilizing container shown in FIG. 5.

When the endoscope 2 is housed in the sterilizing container 34 for the high-temperature and pressure steam sterilization, the sterilizing container 34 is generally accommodated (packed) in a sterilizing package (such as a peel pack). Plural ventilation holes (steam entrance holes) not shown are formed on the tray 35 and the lid member 36 of the sterilizing container 34 to allow passage of the steam.

The sterilizing package, however, is generally formed from a film surface which does not allow passage of the steam and a filter surface which allows passage of the steam. When the film surface adheres to the ventilation holes (steam entrance hole) of the tray 35 or the lid member 36, the film surface closes the ventilation holes to prevent the entrance of the steam into the sterilizing container, thereby affecting the sterilization effect.

The present embodiment allows for the speedy and secure sterilization without the obstruction of steam entrance into the sterilizing container even when the sterilizing container 34 is housed (packed) and sealed in the sterilizing package. The embodiment will be described below with reference to FIG. 5.

As shown in FIG. 5, in the endoscopic system according to the present embodiment, the endoscope 2 is housed in the sterilizing container 34, and the sterilizing container 34 is accommodated and sealed in a sterilizing package 51, and then, the sterilizing package 51 is put into a chamber in the high-temperature and pressure steam sterilization apparatus for the high-temperature and pressure steam sterilization treatment.

The sterilizing package 51 has a transparent film surface 51A which has a characteristic of not allowing the passage of the steam, and a filter surface (e.g., paper filter) 51B (also referred to as a steam-permeable filter) which has a characteristic of allowing the passage of the steam. When the film surface 51A and the filter surface 51B are attached with each other at respective edges, a bag-like package can be formed so as to be able to pack the sterilizing container in a sealed state. Though FIG. 5 shows an example of the sterilizing package 51 formed only from the film surface 51A and the filter surface 51B, the structure of the sterilizing package is not necessarily limited to the structure of FIG. 5. As far as the film surface 51A and the filter surface 51B are provided at least in one portion of an external surface of the sterilizing package 51, any structures can function as the sterilizing package.

The tray 35 and the lid member 36 of the sterilizing container 34 have plural ventilation holes 50 at positions where the filter surface 51B does not touch when the sterilizing container 34 is packed in the sterilizing package 51.

In other words, the tray 35 has plural ventilation holes 50 at least on a part of the surface thereof, or on every surface. Similarly to the tray 35, the lid member 36 has plural ventilation holes 50 at least on a part of the surface thereof, or on every surface.

Here, the ventilation holes 50 may be provided not only on the side surfaces of the tray 35 and the lid member 36, but also on the upper surface of the lid member 36 or on the bottom surface of the tray 35. The structure of the sterilizing container 34 is substantially the same as that of the first embodiment described above.

Advantageous effects of the present embodiment will be described. Assume that the endoscope 2 of the present embodiment is housed in the sterilizing container 34, which is further packed in the sterilizing package 51, and that the sterilizing package 51 is put into the chamber for the high-temperature and pressure steam sterilization. Here, the sterilizing package 51 is positioned on a bottom surface 52A of the chamber as shown in FIG. 5.

When the high-temperature and pressure steam sterilization treatment is performed in the chamber, the steam passes through the filter surface 51B of the sterilizing package 51 to enter into the sterilizing package 51. Thereafter, the steam passes through the plural ventilation holes 50 provided on the lid member 36 and the tray 35 to enter the sterilizing container 34. Thereafter, with the process similar to the first embodiment, the steam fills the inside and the outside of the channels of the endoscope 2 and the high-temperature and pressure steam sterilization treatment is performed swiftly.

Even if the film surface 51A of the sterilizing package 51 adheres to the upper surface of the lid member 36 by the pressure applied by the sterilization treatment, for example, since the ventilation holes 50 are formed on the side surface of the lid member 36, the ventilation holes 50 are not closed and the steam can enter the sterilizing package 51. In other respects, the second embodiment has the similar advantages to the first embodiment.

Therefore, according to the second embodiment, even when the endoscope 2 is housed in the sterilizing container 34 which is further housed (packed) and sealed in the sterilizing package, the entrance of the steam into the sterilizing container 34 is not obstructed and the sterilization can be swiftly performed without fail.

FIG. 6 shows a modified example of the first embodiment where a sufficient amount of steam can enter the sterilizing package 51 even when the film surface 51A adheres to the side surface of the lid member 36 on which plural ventilation holes 50 are formed.

As shown in FIG. 6, in the sterilizing container 34 of the modified example, plural pits 50A are formed on the side surface of the lid member 36, and ventilation holes 50a are formed respectively in the pits 50A. In such a structure, even when the film surface 51A sticks to the side surface of the lid member 36, a clearance is formed between the film surface 51A and the pit 50A, whereby the ventilation holes 50a are not closed and a sufficient amount of steam can enter the sterilizing package 51.

The structure described in the present embodiment has plural pits 50A each having the ventilation hole 50a and provided on the side surface of the lid member 36. The structure may be formed so that plural pits each having the similar ventilation hole 50a are formed on the bottom surface of the tray 35. Such structure is advantageous in that the filter characteristic of the filter surface 51B can be enhanced.

Figure 7:
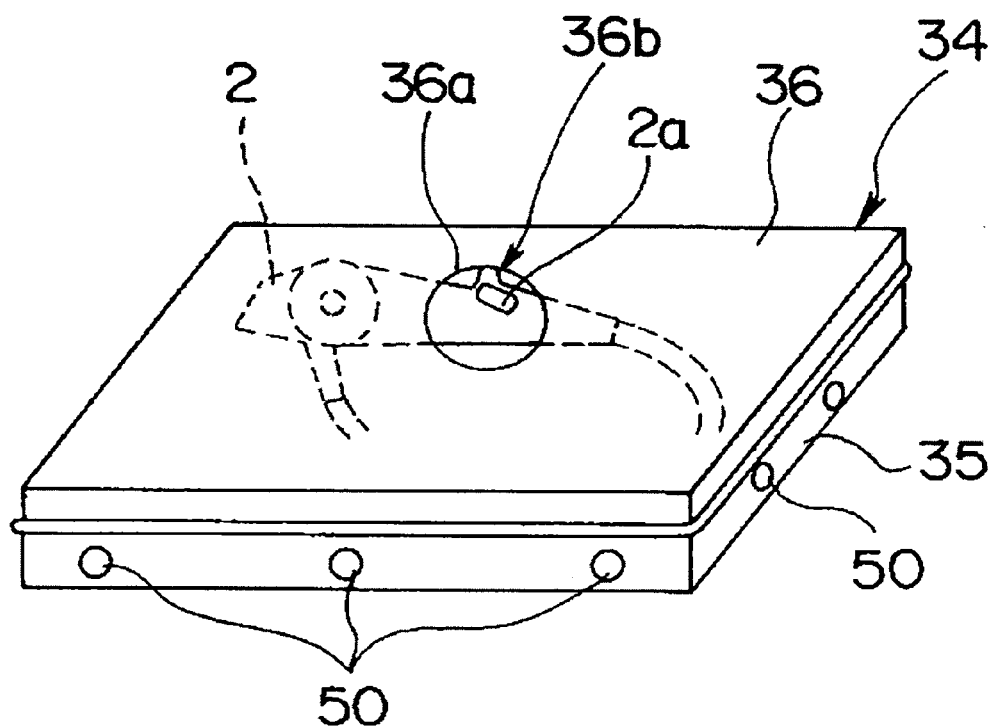
FIG. 7 is a schematic view of a structure of a sterilizing container used in an endoscopic system according to a third embodiment of the present invention.
Figure 8:
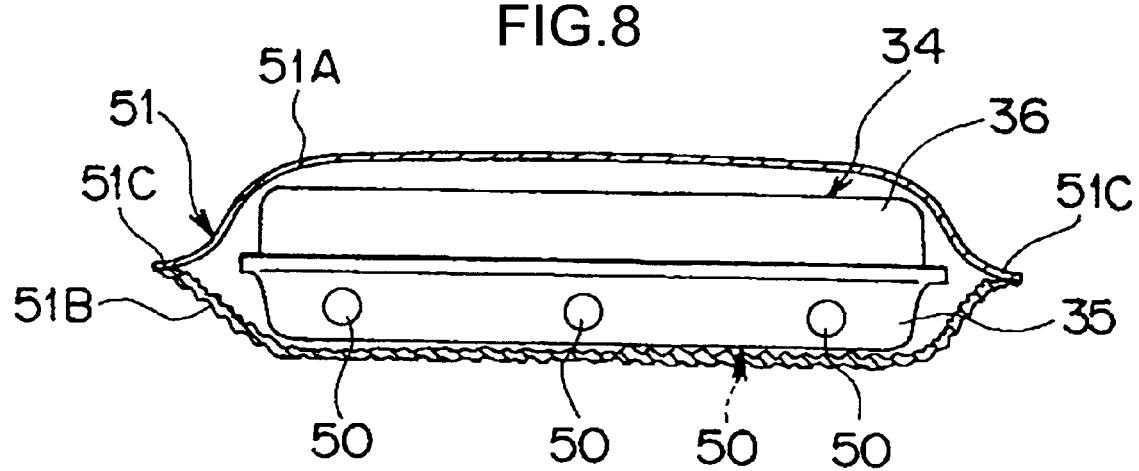
FIG. 8 is a schematic view of the sterilizing container housed in a sterilizing package.

FIGS. 7 and 8 show an endoscopic system according to a third embodiment of the present invention. FIG. 7 is a schematic view of a structure of a sterilizing container used in the endoscopic system, and FIG. 8 is a schematic view of the sterilizing container housed in a sterilizing package. FIGS. 9 and 10 show a modified example of the third embodiment. FIG. 9 is a schematic view of the sterilizing package of FIG. 8 placed in a chamber, and FIG. 10 is a perspective view of an example of a base member of FIG. 9.

As shown in FIG. 7, in the endoscopic system according to the present embodiment, a display 36b for confirmation is provided on the lid member 36 of the sterilizing container 34, so that the endoscope 2 housed in the tray 35 can be visually confirmed. The display 36b for confirmation is formed by, for example, attaching a transparent member (not shown) formed from a transparent member which endures the high-temperature and pressure steam over an opening 36a of the lid member 36 provided at a position corresponding to the main parts of the endoscope 2 housed in the tray 35.

The display 36b for confirmation may be formed by detachably attaching the transparent member (not shown), or only by providing the opening 36a without attaching the transparent member. Alternatively, the lid member 36 may be entirely formed from a transparent member.

In the present embodiment, a sheet-like chemical indicator (or a biological indicator) 2a is pasted onto the endoscope 2 housed in the tray 35 for the confirmation of the sterilizing effect by the high-temperature and pressure steam sterilization at a corresponding position to the position of the display 36b for confirmation.

Further, similarly to the second embodiment, the plural ventilation holes 50 are formed on the side surface of the tray 35, and still further, plural ventilation holes 50 are formed on the bottom surface of the tray 35 though not shown.

In the present embodiment, as shown in FIG. 8, when the high-temperature and pressure steam sterilization is to be performed, the endoscope 2 is housed in the sterilizing container 34 with the above-described structure, and the sterilizing container 34 is put into the sterilizing package 51 similarly to the second embodiment, and then the sterilizing package 51 is put into the chamber and the high-temperature and pressure steam sterilization is performed. In other respect, the structure of the present embodiment is the same as those of the first and the second embodiments.

Advantageous effects of the display 36b for confirmation according to the present embodiment will be described. As shown in FIG. 8, the sterilizing container 34 is housed in the sterilizing package 51 and then together put into the chamber for the high-temperature and pressure steam sterilization. Then, after the high-temperature and pressure steam sterilization is completed, the sterilizing package 51 subjected to the high-temperature and pressure steam sterilization is taken out from the chamber.

Here, the film surface 51A of the sterilizing package 51 is transparent, and the transparent display 36b for confirmation is provided on the lid member 36 of the sterilizing container 34 housed inside the sterilizing package 51. Therefore, the operator can visually confirm the state of the endoscope 2 housed inside the tray 35 without opening the sterilizing package 51 and the lid member 36 to take out the endoscope 2. In other words, since the operator can visually confirm the chemical indicator 2a pasted onto the endoscope 2, the operator can confirm the sterilizing effect on the endoscope 2 by the high-temperature and pressure steam sterilization by observing the chemical indicator 2a.

Thus, similar advantages as obtained in the first embodiment can be obtained in the present embodiment. In addition, the state of the housed endoscope 2 can be visually confirmed without opening the sterilizing package 51 or the sterilizing container 34 after the completion of the high-temperature and pressure steam sterilization, and further, if the chemical indicator is pasted onto the endoscope 2, the sterilizing effect on the endoscope 2 can also be confirmed.

FIGS. 9 and 10 show a modified example of the third embodiment. Generally, when the high-temperature and pressure steam sterilization is performed, the sterilizing container 34 housing the endoscope 2, or the sterilizing package 51 housing the sterilizing container 34 is put into the chamber. For a more speedy high-temperature and pressure steam sterilization, it is desirable that the shape and the size of the chamber is adjusted to the shape and the size of the sterilizing container 34 or the sterilizing package 51 as far as possible.

When the chamber is structured as mentioned above, however, the filter surface 51B of the sterilizing package 51 may adhere to the bottom surface of the tray 35, thereby closing the ventilation holes 50 provided on the bottom surface. Then such structure may negatively affect the entrance of the steam into the tray 35.

Hence, in the modified example, as shown in FIG. 9, a base member 53 (also referred to as a ventilating unit) on which the sterilizing package 51 is placed is provided on the bottom surface of the chamber 52. The base member 53 is, for example, a net-like plate as shown in FIG. 10 and has plural legs 53a provided on the bottom surface of the plate.

Thus, when the base member 53 is provided, even when the filter surface 51B adheres to the bottom surface of the tray 35 so as to close the ventilation holes 50 on the bottom surface, the legs 53a of the base member 53 serve to provide clearance between the bottom surface of the tray 35 and the bottom surface of the chamber 52. In addition, since the base member 53 is formed like a net, the steam can enter into the tray 35 via the bottom surface (ventilating holes) of the tray 35.

Thus, since the chamber 52 can be formed in the size and the shape corresponding to the size and the shape of the sterilizing package 51 and the sterilizing container 34 so as to eliminate unnecessary spaces, the high-temperature and pressure steam sterilization can be performed more swiftly without fail.

It should be noted that the present invention is not limited to the embodiments and modified examples as described above and can be variously altered within a scope not departing from a gist of the present invention.

What is claimed is:

1. An endoscopic system comprising:
    an endoscope having openings to communicate with an inner region of the endoscope;
    a sterilizing container that is adapted to house the endoscope and that has a plurality of pits on at least a side surface of the sterilizing container, and ventilation holes for communicating with an outside space of the sterilizing container, said ventilation holes being formed respectively in the pits; and
    a sterilizing package which is formed from a steam-permeable filter and an optically-transparent film in at least one portion of an outer periphery of the sterilizing package, and is adapted to house the sterilizing container inside at the time of autoclave sterilization such that the optically-transparent film faces to the ventilation holes, wherein in the sterilizing container,
        a plurality of gap portions of predetermined volumes are formed at positions to which the openings face when the endoscope is housed in the sterilizing container, and
        a steam entrance path, which communicates the gap portions with an outside space of the sterilizing container, is formed so as to guide steam fed from the outside space at the sterilization to the inner region of the endoscope via the gap portions and the openings; and
        a cross-sections area of each of the gap portions and the steam entrance path in a plane perpendicular to an entering direction of the steam is equal to or larger than a cross-sections area of each of the openings.

2. The endoscopic system according to claim 1, wherein the openings comprise:
    channel openings, each of which communicates with a predetermined channel formed inside the endoscope; and
    a ventilating opening that serves to communicate an external surface of the channel with the outside space of the endoscope, and
    the gap portions are formed corresponding to the channel openings and the ventilating opening.

3. The endoscopic system according to claim 2, wherein the ventilating opening is formed on an electrical connector which electrically connects internal electric circuitry with an external device.

4. The endoscopic system according to claim 2, wherein the endoscope includes an insertion to be inserted into an object at a time of use, and an operating unit located outside the object and used for a manipulation by a user of the endoscope, and
    the ventilating opening is formed on a partial region of the operating unit.

5. The endoscopic system according to claim 2 wherein the endoscope includes an insertion to be inserted into an object at a time of use, and an operating unit located outside the object and used for a manipulation by a user of the endoscope, and
    the channel openings are formed on a tip end of the insertion and a partial region of the operating unit.

6. The endoscopic system according to claim 1, further comprising
   an autoclave sterilizing apparatus including
      a chamber that houses the sterilizing package at the time of the autoclave sterilization so that the optically-transparent film is located at a vertically upward side and the steam-permeable filter is located at a vertically downward side, and
      a ventilating unit that secures a ventilating state between the steam-permeable filter forming the sterilizing package and an inside space of the chamber, and that is located below the sterilizing package so that the ventilating unit is in contact with the vertically downward side of the sterilizing package at the time of the autoclave sterilization in the chamber, wherein
   the sterilizing container includes a visual confirmation unit that allows visual confirmation of the endoscope housed in the sterilizing container and that is provided at the vertically upward side, and
   the sterilizing container is housed in the sterilizing package so that the endoscope can be visually confirmed from outside at the time of the autoclave sterilization via the visual confirmation unit and the optically-transparent film arranged on the vertically upward side of the sterilizing package.

7. The endoscopic system according to claim 6, wherein the ventilating unit includes
   a net member that is arranged in contact with a lower surface of the sterilizing package, and
   a leg that secures a gap between the net member and a bottom portion of the chamber.

8. The endoscopic system according to claim 6, wherein the visual confirmation unit is formed by providing a predetermined opening or by providing a transparent member on the predetermined opening.

9. The endoscopic system according to claim 6, wherein the endoscope includes a chemical indicator that displays a sterilization effect by the autoclave sterilization at a position which can be visually recognized from outside via the visual confirmation unit when the endoscope is housed in the sterilizing container.

* * * * *